(12) United States Patent
Stallings et al.

(10) Patent No.: US 6,776,791 B1
(45) Date of Patent: Aug. 17, 2004

(54) STENT AND METHOD AND DEVICE FOR PACKING OF SAME

(75) Inventors: Jody W. Stallings, Clearwater, FL (US); Frederick Ahari, Clearwater, FL (US)

(73) Assignee: Endovascular Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/434,962

(22) Filed: Nov. 5, 1999

Related U.S. Application Data (62) Division of application No. 09/053,393, filed on Apr. 1, 1998, now abandoned.

(51) Int. Cl.[7] .................................................. A61F 2/06
(52) U.S. Cl. ..................................... 623/1.11; 623/1.12
(58) Field of Search ........................ 623/1.11; 606/194, 606/195, 198, 140, 141, 208; 600/36; 604/15, 93.01, 96.01

(56) References Cited

U.S. PATENT DOCUMENTS

| | | | | |
|---|---|---|---|---|
| 3,958,576 A | * | 5/1976 | Komiya ....................... 128/346 |
| 4,617,932 A | * | 10/1986 | Kornberg .................... 128/334 |
| 4,875,480 A | * | 10/1989 | Imbert ........................ 128/343 |
| 5,387,235 A | * | 2/1995 | Chuter ............................ 623/1 |
| 5,554,181 A | * | 9/1996 | Das ............................ 623/1.15 |
| 5,593,442 A | | 1/1997 | Klein |
| 5,693,083 A | * | 12/1997 | Baker et al. .................... 623/1 |
| 5,733,325 A | | 3/1998 | Robinson et al. |
| 5,776,181 A | | 7/1998 | Lee et al. |
| 5,800,515 A | | 9/1998 | Nadal et al. |
| 5,824,036 A | | 10/1998 | Lauterjung |
| 5,824,055 A | * | 10/1998 | Spiridigliozzi et al. ........ 623/1 |
| 5,843,167 A | | 12/1998 | Dwyer et al. |
| 5,853,419 A | | 12/1998 | Imran |
| 5,910,144 A | * | 6/1999 | Hayashi ...................... 606/108 |
| 6,187,016 B1 | * | 2/2001 | Hedges et al. .............. 606/108 |

* cited by examiner

*Primary Examiner*—Corrine McDermott
*Assistant Examiner*—Alvin Stewart
(74) *Attorney, Agent, or Firm*—Fulwider Patton Lee & Utecht, LLP (57) ABSTRACT

A method for inserting a stent into the delivery sheath of a stent/graft deployment catheter. The stent has V hooks on its proximal end which are positively engageable by projections attached to a stent/graft deployment catheter plunger. The proximal end of the stent is manually squeezed over the V hooks such that the V hooks engage the projections. The catheter is passed through the center of a funnel. While maintaining pressure on the stent and the V hooks, the plunger is withdrawn so as to pull the stent into the delivery sheath through the center of the funnel. The funnel guides the stent into the delivery sheath and gradually compresses the stent as it approaches the delivery sheath.

34 Claims, 6 Drawing Sheets

STENT AND METHOD AND DEVICE FOR PACKING OF SAME

This is a divisional application of Ser. No. 09/053,393 filed Apr. 1, 1998, now abandoned.

BACKGROUND OF THE INVENTION

1. Field of the Invention

The invention relates to an improved stent and stent/graft deployment catheter. More particularly, the invention relates to a stent which is capable of being loaded into the delivery sheath of a stent/graft deployment catheter without suffering any structural damage and which is uniformly radially compressed during packing.

2. Description of the Prior Art

An abdominal aortic aneurysm (AAA) is a sac caused by an abnormal dilatation of the wall of the aorta as it passes through the abdomen. The aorta is the main artery of the body, supplying blood to all organs and parts of the body except the lungs. It arises from the left ventricle of the heart, passes upward, bends over and passes down through the thorax and through the abdomen, and finally divides into the iliac arteries which supply blood to the pelvis and lower extremities.

The AAA ordinarily occurs in the portion of the aorta below the kidneys. When left untreated, the aneurysm will eventually cause the sac to rupture with ensuing fatal hemorrhaging in a very short time. The repair of abdominal aortic aneurysms has typically required major abdominal surgery in which the diseased and aneurysmal segment of the aorta is bridged with a prosthetic device, such as a synthetic graft.

As with all major surgeries, there are many disadvantages to the above mentioned surgical technique, the foremost of which is the high mortality and morbidity rate associated with surgical intervention of this magnitude. Other disadvantages of conventional surgical repair include the extensive recovery period associated with such surgery; difficulties in suturing the graft to the aorta; the unsuitability of the surgery for many patients, particularly older patients exhibiting comorbid conditions; and the problems associated with performing the surgical procedure on an emergency basis after the aneurysm has already ruptured.

In view of the above mentioned disadvantages of conventional surgical repair techniques, techniques have been developed for repairing AAAs by intraluminally delivering an aortic graft to the aneurysm site through the use of a catheter based delivery system, and securing the graft within the aorta using an expandable stent. Since the first documented clinical application of this technique was reported by Parodi et al. in the Annals of Vascular Surgery, Volume 5, pages 491–499 (1991), the technique has gained more widespread recognition and is being used more commonly.

Problems have been encountered accurately deploying the stent/graft. These problems are partially due to the method of packing the stent/graft into the delivery sheath of the deployment catheter. Currently, the stent/graft is manually radially compressed and pushed into the delivery sheath. This stent/graft compress and push method is problematic for a number of reasons. First, this process often leads to breakage of the stent struts. A stent with broken struts may not expand as designed, and as a result, will not properly bridge the AAA upon deployment. Second, this compress and push method of stent/graft packing produces a non-uniformly compressed stent. Unless all of the stent cells are equally compressed the stent/graft may not expand as designed upon exposure to the patient's blood, and as a result, the stent/graft will not adequately bridge the AAA. Another drawback of the present compress and push method of stent/graft packing is that it is very time consuming and difficult, and therefore, it is inappropriate for large scale production.

Therefore, the need exists for an improved method for inserting a stent/graft into the delivery sheath of a deployment catheter. Furthermore, the need exists for an improved stent and a stent/graft deployment catheter which is capable of being loaded with a stent/graft using the improved stent/graft packing method.

SUMMARY OF THE INVENTION

Accordingly, it is an object of the invention to produce a method for inserting a stent/graft which overcomes the deficiencies of the prior art compress and push packing method.

It is another object of the invention to produce a stent/graft deployment catheter capable of pulling a uniformly compressed stent/graft into its delivery sheath without damaging the stent/graft.

It is a further object of the invention to produce a stent with V hooks capable of being pulled into the delivery sheath of the stent/graft deployment catheter.

The invention is a method for inserting an improved stent into the delivery sheath of an improved stent/graft deployment catheter. The stent has V hooks on its proximal end which are positively engageable by projections attached to a stent/graft deployment catheter plunger. The proximal end of the stent is manually squeezed over the V hooks such that the V hooks engage the projections. The catheter is passed through the center of a funnel. While maintaining pressure on the stent and the V hooks, the plunger is withdrawn so as to pull the stent into the delivery sheath through the center of the funnel. The funnel guides the stent into the delivery sheath and uniformly compresses the stent as it approaches the delivery sheath.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
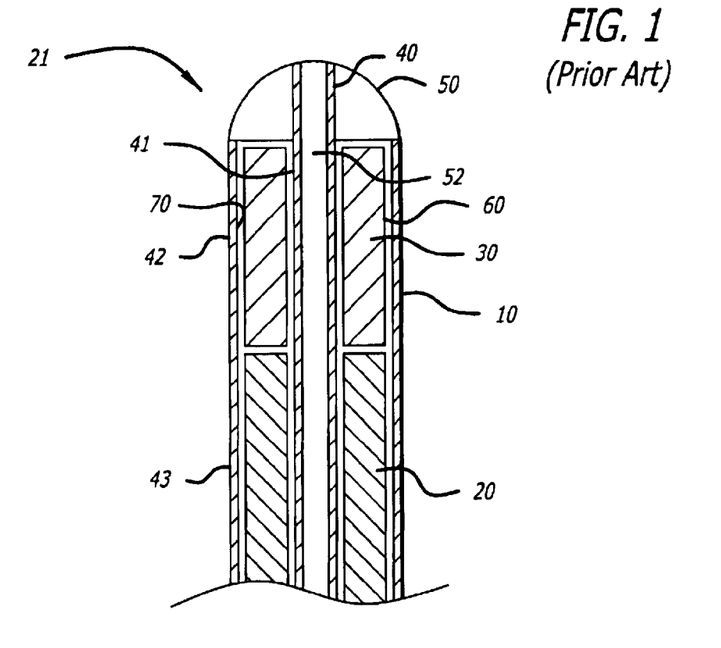
FIG. 1 is longitudinal cross section of a distal portion of a prior art stent/graft deployment catheter.

FIG. 1 illustrates a longitudinal cross section of a co-axial prior art stent/graft deployment catheter 21. Said catheter 21 is comprised of a catheter body 10, a tip 50, an inner tube 40, a stent/graft 30, and a plunger 20, all of which are co-axial and have proximal and distal ends. Only the distal portion of the deployment catheter 21 is shown for clarity. The catheter body 10 is slidingly disposed about the inner tube 40 and has a delivery sheath 42, a tube portion 43, and an inner surface 70. The plunger 20 is slidingly disposed about the inner tube 40 and is slidingly disposed within the catheter body 10. The distal end of the inner tube 40 is attached to the tip 50. The stent/graft 30 is slidingly disposed about the inner tube 40 and within the delivery sheath 42 of the catheter body 10 and is between the proximal end of the tip 50 and the distal end of the plunger 20. The stent/graft 30 has an outer surface 60 and a lumen 52 extending from its proximal end to its distal end. The stent/graft lumen 52 is occupied by a distal portion 41 of the inner tube 40. The delivery sheath 42 is located between the tip 50 and the tube portion 43 of the catheter body 10. The inner and outer diameters of the delivery sheath 42 and the tube portion 43 are the same.

Figure 2:
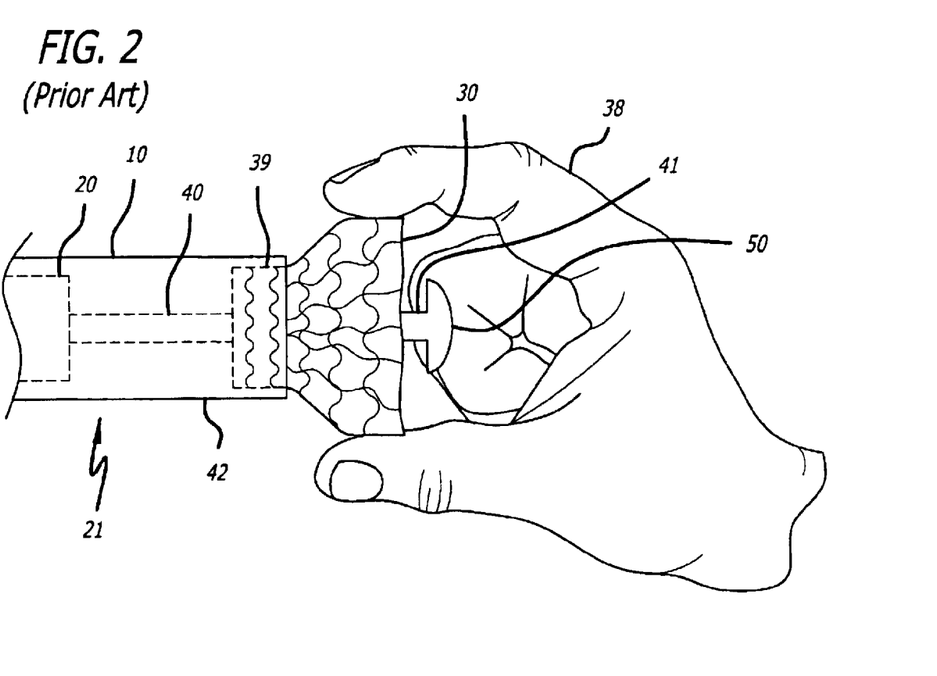
FIG. 2 is a plan view of a stent/graft being inserted into a delivery sheath via the prior art compress and push packing method.

FIG. 2 illustrates a perspective view of the stent/graft 30 being inserted by hand 38 into the delivery sheath 42 via the prior art compress and push method. The plunger 20, the inner tube 40, and a proximal portion 39 of the stent/graft 30 can be seen through the delivery sheath 42 wall as dotted lines. The catheter body 10 has been pulled back exposing the distal portion 41 of the inner tube 40. The stent/graft 30 is disposed about the distal portion 41 of the inner tube 40 as is pinched by hand 38 and pushed into the delivery sheath 42. The stent/graft 30 is made from a shape memory alloy, such as Nitinol, and is cooled below its transformation temperature allowing it to be compressed without permanent structural damage.

Figure 3:
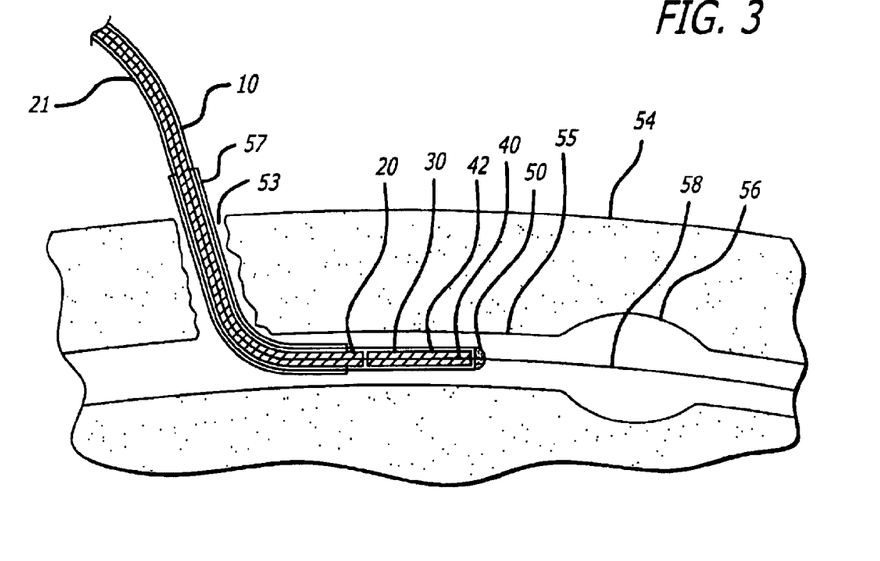
FIG. 3 illustrates a longitudinal cross section of the prior art catheter of FIG. 1 percutaneously inserted into a patient's blood vessel.

The stent/graft deployment catheter 21 may be inserted percutaneously or via a surgical cut-down method into a blood vessel. FIG. 3 illustrates a longitudinal cross section of the prior art catheter 21 percutaneously inserted in a blood vessel 55 of a patient 54. The delivery sheath 42 is still downstream of an aneurysm 56 in need of repair and has fully exited an insertion sheath 57. If inserted percutaneously, as illustrated in FIG. 3, a guide wire 58 is first advanced through an insertion site 53 into the blood vessel 55 of the patient 54. Next, a dilator sheath assembly (dilator not shown) is disposed about the guide wire 58 and the distal portion of the dilator is used to dilate the insertion site 53. After dilation of the insertion site 53 the dilator is removed while the insertion sheath 57 is held in place in the blood vessel 55 of the patient 54. Next, the catheter 21 is inserted into the introducer sheath 57 and is advanced forward into the blood vessel 55 of the patient 54. Upon proper positioning of the tip 50 in the blood vessel 55 the plunger 20 is held in place while the catheter body 10 is pulled away from the tip 50 exposing the entire stent/graft 30 to blood. Upon contact with blood the stent/graft 30 expands such that the diameter of the stent/graft lumen 52 becomes larger than the outer diameter of the tip 50. The expanded stent/graft 30 becomes fixed in place in the blood vessel 55 and thus bridges the aneurysm 56. The inner tube 40 is then pulled away from the stent/graft 30 such that the tip 50 passes through the stent/graft lumen 52. Finally, the catheter 21 is removed from the patient 54. Note that there are many other types of self-expandable stent/grafts on the market including heat sensitive and spring-like stent/grafts. Note further that one major function of the introducer sheath 57 is to control bleeding at the insertion site 53 of the patient 54 during the entire procedure.

Figure 4:
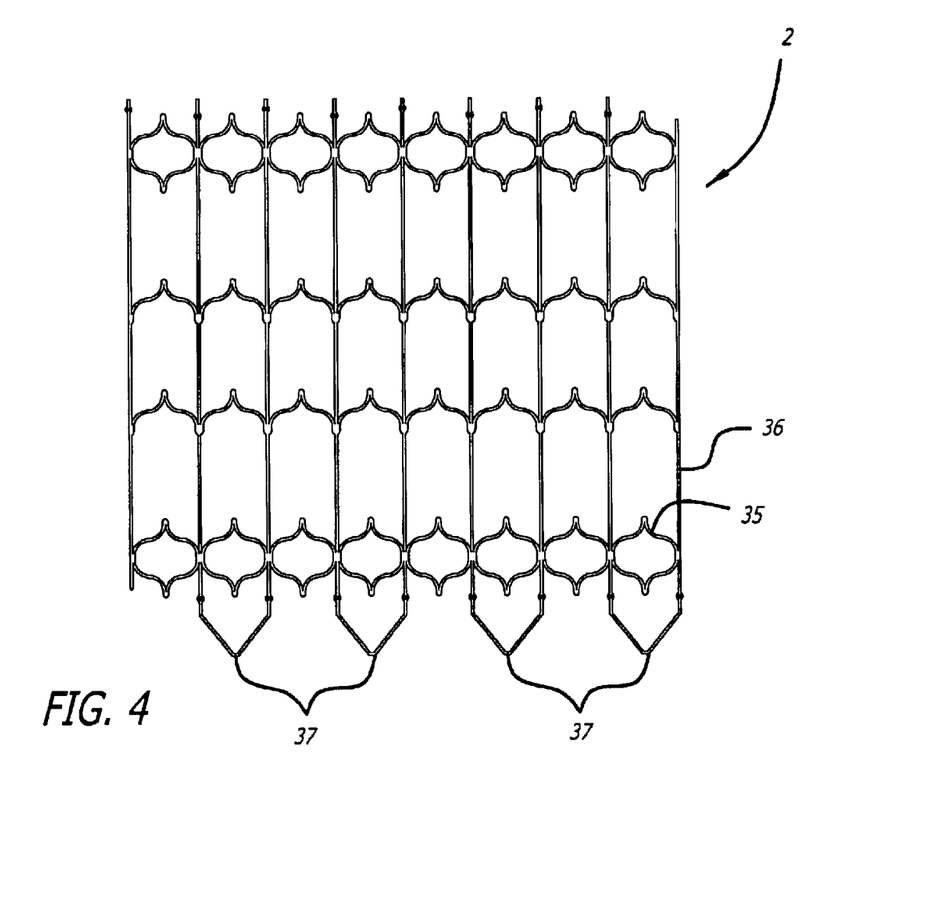
FIG. 4 is a plan view of an unrolled stent having four V hooks.
Figure 5:
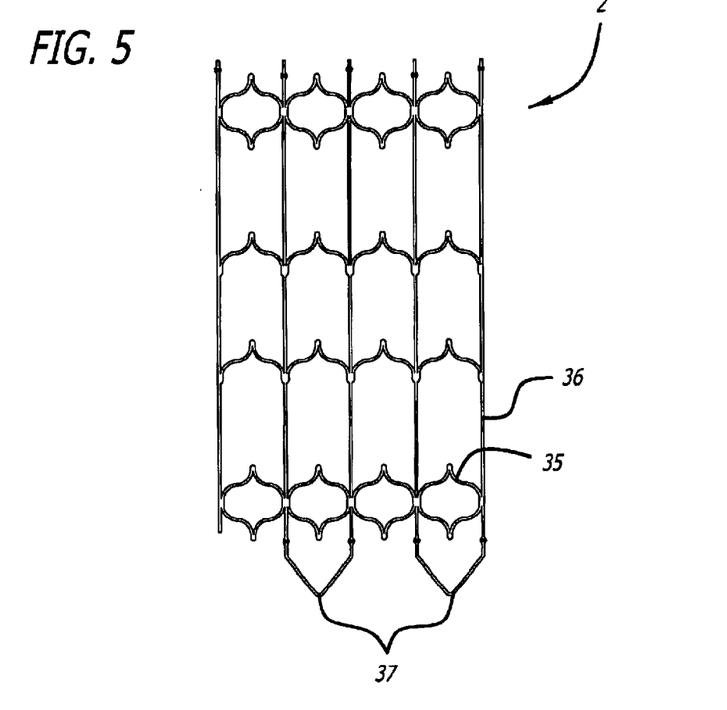
FIG. 5 is a plan view of an unrolled stent having two V hooks.

The prior art compress and push packing method may damage the stent/graft 30 and produce a non-uniformly compressed stent which may not adequately bridge the aneurysm 56 upon deployment. FIG. 4 illustrates a plan view of an unrolled improved stent 2 having four V hooks 37 which is capable of being inserted in a uniformly compressed state and without structural damage. The stent 2 comprises nine parallel struts 36 which are connected by heart shaped cross members 35. Each V hook 37 is connected to the end of two adjacent struts 36. Stents that are 20 mm in diameter or greater generally require at least four V hooks for proper insertion into a delivery sheath. Stents that are less than 20 mm in diameter only require two V hooks. An unrolled stent 2 having only two V hooks 37 is illustrated in FIG. 5.

Figure 6:
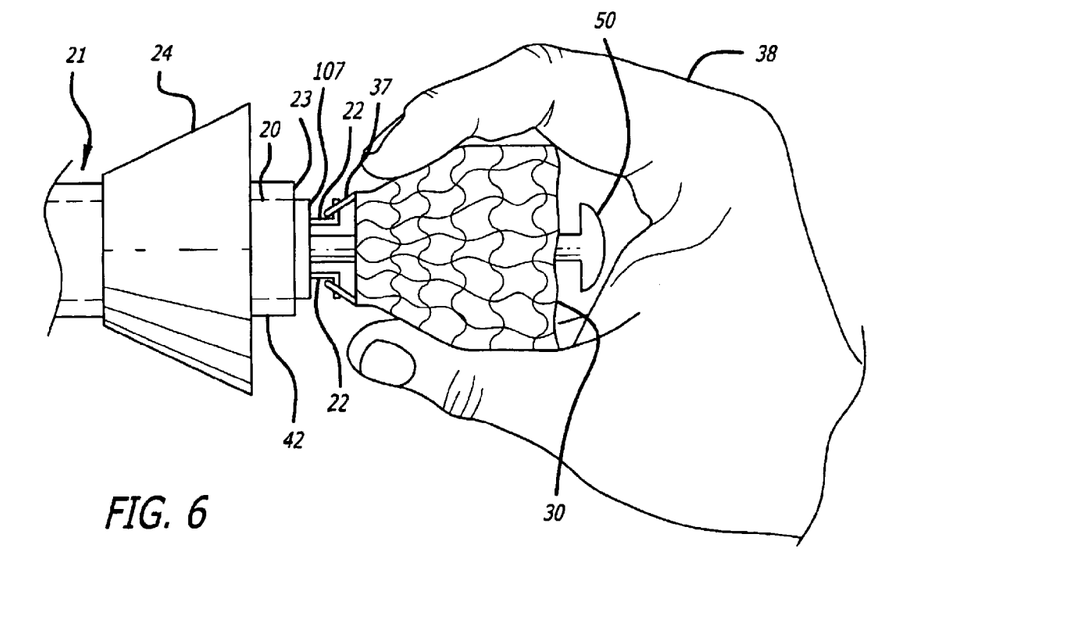
FIG. 6 is perspective view of a stent/graft being compressed so as to positively engage the stent's V hooks with a plunger's L projections.
Figure 7:
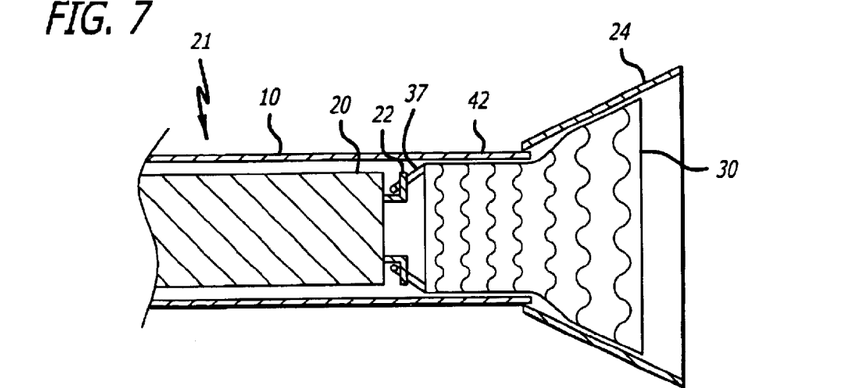
FIG. 7 is a longitudinal cross section of a stent/graft which is partially inserted in a delivery sheath and partially enveloped by a funnel.
Figure 8:
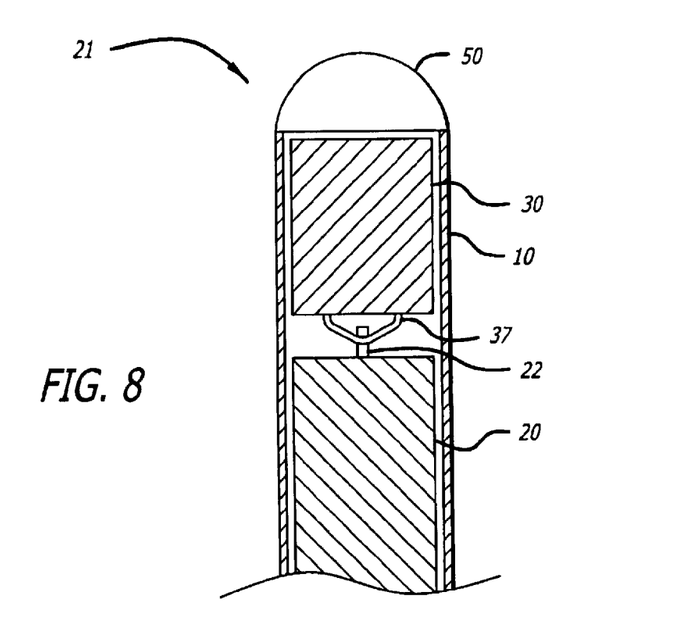
FIG. 8 is a longitudinal cross section of a stent/graft having V hooks fully compressed and inserted into a delivery sheath.

FIGS. 6–8 illustrate the improved method of packing the improved stent 2 (shown in FIG. 5) using an improved stent/graft deployment catheter 21 having two L projections 22 projecting from a distal end 107 of the plunger 20. As can be seen in FIG. 6, the improved stent/graft deployment catheter 21 is first advanced through the center of a funnel 24. The catheter body 10 is then pulled back exposing the distal portion 41 of the inner tube 40 and a distal portion 23 of the plunger 20. The remaining portion of the plunger 20 is disposed within the catheter body 10 and is shown as dotted lines. Next, the L projections 22 are placed between the V hooks 37. The stent/graft 30 is the compressed lightly by hand 38 such that the V hooks 37 are positively engaged by the L projections 22. While maintaining said engagement the catheter 21 is moved to the left, relative to the catheter body 10, such that the stent/graft 30 contacts the funnel 24. Next, while holding the catheter body 10, the plunger 20 is moved to the left forcing the stent/graft 30 into the delivery sheath 42. As soon as the portion of the stent/graft 30 immediately to the right of the V hooks 37 is enveloped by the delivery sheath 42 the hand 38 releases the stent/graft 30. The plunger 20 is pulled until the entire stent/graft 30 is disposed within the delivery sheath 42, as illustrated in FIG. 8. FIG. 8 illustrates a longitudinal cross section of a distal portion of the improved stent/deployment catheter 21 without the inner tube 40 after the stent/graft 30 has been completely inserted. Note that the stent/graft 30 may be made from a shape memory alloy, such as Nitinol. Prior to packing a shape memory alloy stent/graft, the body of the stent/graft must be cooled below its transformation temperature in order to allow it to be compressed without incurring any structural damage.

FIG. 7 illustrates a longitudinal cross section of the stent/graft 30 partially inserted in the delivery sheath 42 and partially enveloped by the funnel 24. The V hooks 37 are positively engaged by the L projections 22. The funnel 24 guides the stent/graft 30 into the delivery sheath 42. As the plunger 20 is moved left relative to the catheter body 10, the funnel 24 uniformly compresses the stent/graft 30.

Figure 9:
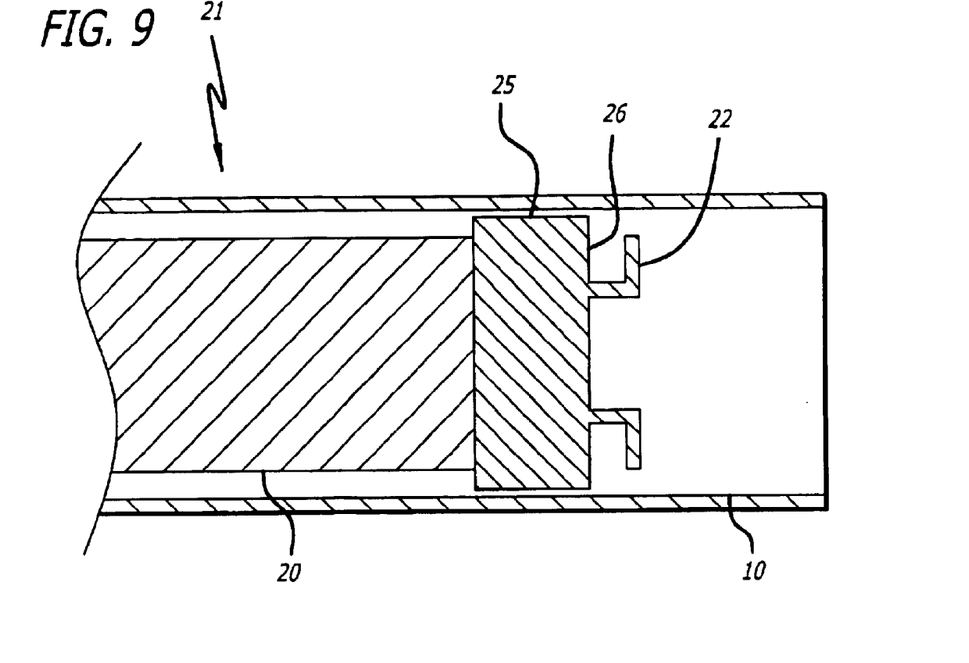
FIG. 9 illustrates a longitudinal cross section of a stent/graft deployment catheter having a grabber housing and without the inner tube and the tip.
Figure 10:
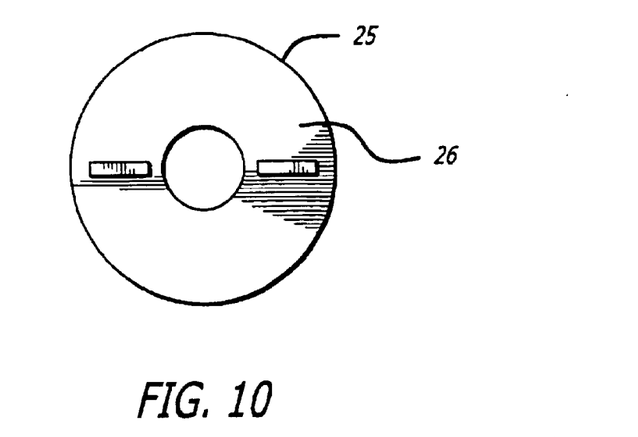
FIG. 10 illustrates a plan view of a distal surface of the grabber housing of FIG. 9.

An alternate embodiment of the invention involves adding a component to the catheter 21 rather than altering the plunger 20 itself. FIG. 9 illustrates a longitudinal cross section of a distal portion of a stent/graft deployment catheter 21 without the inner tube 40 (shown in FIG. 6) and the tip 50 (shown in FIG. 6). A grabber housing 25 is attached to the distal end of the plunger 20 and is disposed about the inner tube 40. The grabber housing 25 has two L projections projecting from a distal surface 26. The stent/graft 30 is inserted in the same manner as illustrated in FIGS. 6–8. FIG. 10 illustrates a plan view of the distal surface 26 of the grabber housing 25.

Figure 11:
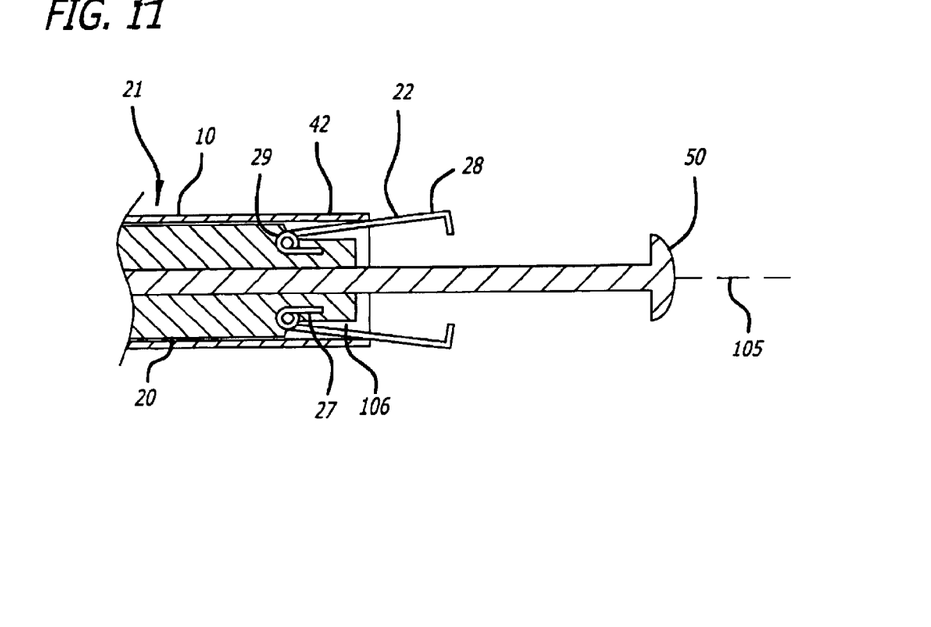
FIG. 11 illustrates a longitudinal cross section of a distal portion of an alternative embodiment of the invention incorporating spring biased projections.
Figure 12:
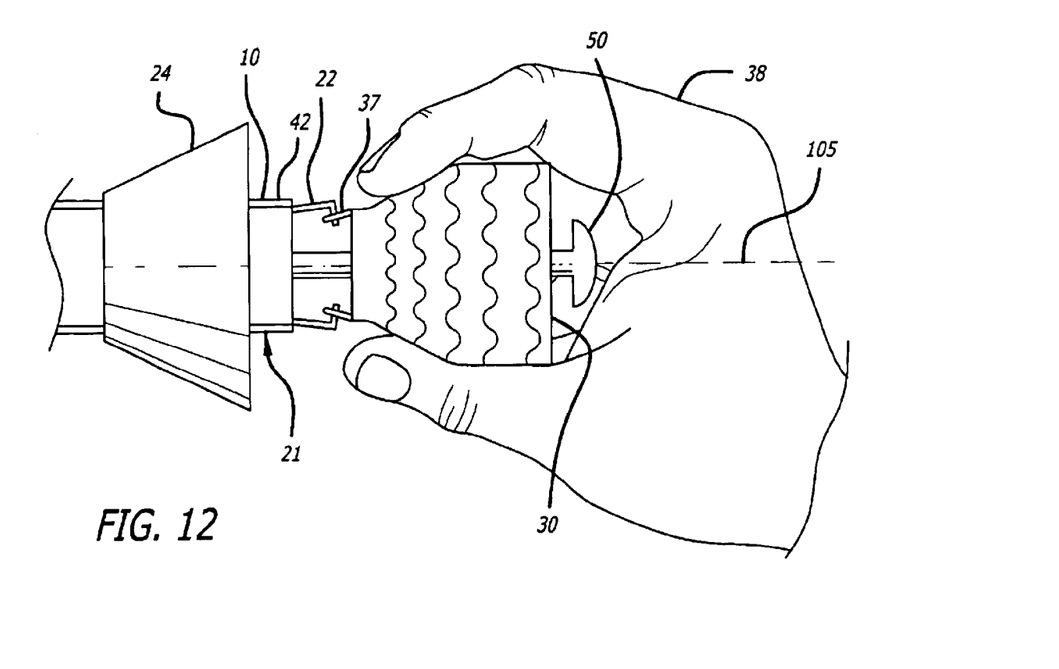
FIG. 12 illustrates a perspective view of a stent/graft being loaded into the delivery sheath of the catheter illustrated in FIG. 11.

An alternate embodiment of the grabber housing 25 or the improved stent/graft deployment catheter 21 may have the L projections 22 inset in the grabber housing 25 or the plunger 20. Alternatively, the L projections 22 may comprise springs attached to the grabber housing 25 or plunger 20, as illustrated in FIG. 11. FIG. 11 illustrates a longitudinal cross section of a distal portion of an alternative embodiment of the invention incorporating spring biased projections. A proximal portion 27 of the L projection 22 is attached to the plunger 20 or to a grabber housing (not shown). A distal portion 28 of the L projection 22 is connected to the proximal portion 27 by a coil portion 29. The coil portion 29 permits the distal portion 28 to move between a position generally parallel to a longitudinal axis 105 of the catheter 21 and a position at an angle to said axis 105 (the equilibrium position). The L projections 22 lie in grooves 106 in the plunger 20 when forced into apposition generally parallel to the axis 105 of the catheter 21. FIG. 12 illustrates a perspective view of a stent/graft 30 being loaded into the delivery sheath 42 of the catheter 21 illustrated in FIG. 11. During packing of the stent/graft 30 into the delivery sheath 42 the plunger 20 is positioned such that the L projections 22 are partially enveloped by the delivery sheath 42. Next, the stent/graft 30 is manually compressed such that the V hooks 37 positively engage the L projections 22. This engagement is accomplished by squeezing the portion of the stent/graft 30 adjacent to the V hooks 37, placing said portion between the L projections 22, and releasing the stent/graft 30 such that the L projections 22 and the V hooks positively engage when the stent/graft 30 partially springs back to its uncompressed state. Next, the plunger 20 is moved to the left relative to the catheter body 10 such that the L projections 22 are forced by the delivery sheath 42 towards the axis 105 of the catheter 21 and such that the delivery sheath 42 envelopes first the L projections 22 and then the stent/graft 30. Note, that unlike the other embodiments of the invention described above, once the V hooks 37 are engaged by the L projections 22 and as long as a sufficient portion of the distal portion 28 is enveloped by the delivery sheath 42, the stent/graft 30 no longer has to be manually compressed to maintain the positive engagement. Once the stent/graft 30 is enveloped by the delivery sheath 42 (after having passed through a funnel 24, as described above) the L projections 22 apply a restoring force against the delivery sheath 42. Upon deployment of the stent/graft 30 said restoring force causes the L projections 22 to spring open, i.e. away from the axis of the catheter 21, disengaging the V hooks 37, and thus, allowing the stent/graft 30 to expand unhindered.

Note that the use of two, three, four or more L projections, in any of the above mentioned embodiments, to engage a multi-hooked stent is contemplated.

What is claimed is:

1. A method for inserting a stent into a deployment catheter, said deployment catheter comprising an outer tube, a plunger at least partially disposed within said outer tube and having a longitudinal dimension, and a stent engagement means connected to a distal end of the plunger for engaging a proximal end of a stent such that the stent engagement means is expandable away from the longitudinal dimension of the plunger, comprising the steps of:
    a) permitting the stent engagement means to expand away from the longitudinal dimension of the plunger;
    b) engaging the stent engagement means and a proximal end of the stent;
    c) cooling the stent; and
    d) moving the plunger and outer tube relative to each other such that the stent is pulled into and disposed within the outer tube;
    wherein the stent engagement means comprises one or more L-shaped hook-like elements.

2. The method as claimed in claim 1 wherein a proximal end of the stent has a catheter engagement means and wherein the stent engagement means engages the catheter engagement means.

3. The method as claimed in claim 2 wherein the catheter engagement means comprises one or more substantially V-shaped elements connected to the proximal end of the stent.

4. The method as claimed in claim 1 further comprising the preliminary step of passing the deployment catheter through a funnel.

5. The method as claimed in claim 1 wherein the stent is made from a shape memory alloy and further comprising the preliminary step of cooling the stent below its transformation temperature prior to moving the plunger and outer tube relative to each other such that the stent is pulled into and disposed within the outer tube.

6. A method for inserting a stent into a deployment catheter, said deployment catheter comprising an outer tube, a plunger at least partially disposed within said outer tube and having a longitudinal dimension, and a stent engagement means connected to a distal portion of the plunger for engaging a proximal end of a stent such that the stent engagement means can expand away from the longitudinal dimension of the plunger, comprising the steps of:
    a) permitting the stent engagement means to expand away from the longitudinal dimension of the plunger;
    b) passing the deployment catheter through the center of a funnel;
    c) cooling the stent;
    d) engaging the stent engagement means and a proximal end of the stent;
    e) while maintaining the engagement of the stent engagement means and the stent, positioning the deployment catheter relative to the funnel such that funnel maintains the engagement of the stent engagement means and the stent; and
    f) moving the plunger and outer tube relative to each other such that the stent is pulled into and disposed within the outer tube.

7. The method as claimed in claim 6 wherein the stent further comprises a catheter engagement means connected to its proximal end and wherein the stent engagement means engages said catheter engagement means.

8. The method as claimed in claim 7 wherein the catheter engagement means comprises substantially V-shaped elements.

9. The method as claimed in claim 8 wherein the stent engagement means comprises one or more hook-like elements connected to a distal portion of the plunger.

10. The method as claimed in claim 9 wherein the stent engagement means and the catheter engagement means are engaged by compressing the proximal end of the stent so as to hook the V-shaped elements onto the hook-like elements such that a force applied to the plunger along the lengthwise axis of the deployment catheter away from a distal end of the deployment catheter pulls the stent in the same direction as the force.

11. The method as claimed in claim 9 wherein the stent comprises a plurality of parallel struts connected by a plurality of connecting members and wherein the catheter engagement means comprises hooks having two ends each of which is attached to the proximal end of an adjacent stent strut.

12. The method as claimed in claim 6 wherein the stent is made from a shape memory alloy and further comprising the step of cooling the stent below its transformation temperature prior to moving the plunger and outer tube relative to each other such that the stent is pulled into and disposed within the outer tube.

13. A stent deployment catheter comprising an outer tube, a plunger at least partially disposed within said outer tube and having a longitudinal dimension, and a stent engagement means being outwardly biased by a coil portion connected to a distal end of the plunger for engaging a proximal end of a stent, the stent engagement means being outwardly biased such that the stent engagement means is configured to expand away from the longitudinal dimension of the plunger, wherein the stent engagement means comprises one or more L-shaped hook-like elements.

14. The stent deployment catheter as claimed in claim 13 wherein the one or more hook-like elements of the stent engagement means are connected to a distal portion of the plunger.

15. The stent deployment catheter as claimed in claim 14 wherein the hook-like elements project from a distal end of the plunger.

16. The stent deployment catheter as claimed in claim 13 wherein the engagement means comprises a tubular body having a distal surface.

17. The stent deployment catheter of claim 13, the stent engagement means further comprising a coiled portion.

18. A method inserting a stent into a deployment catheter, said deployment catheter comprising an outer tube, a plunger at least partially disposed within said outer tube and having a longitudinal dimension, and a stent engagement device connected to a distal end of the plunger that engages a proximal end of a stent the stent engagement device being outwardly biased such that the stent engagement means is expandable away from the longitudinal dimension of the plunger, comprising:
   a) permitting the stent engagement device to expand away from the longitudinal dimension of the plunger;
   b) engaging the stent engagement device and a proximal end of the stent;
   c) cooling the stent; and
   d) moving the plunger and outer tube relative to each other such that the stent is pulled into and disposed within the outer tube;
   wherein the stent engagement device comprises one or more L-shaped hook-like elements.

19. The method as claimed in claim 18 wherein a proximal end of the stent has a catheter engagement device and wherein the stent engagement device engages the catheter engagement device.

20. The method as claimed in claim 19 wherein the catheter engagement device comprises one or more substantially V-shaped elements connected to the proximal end of the stent.

21. The method as claimed in claim 18 further comprising passing the deployment catheter through a funnel.

22. The method as claimed in claim 18 wherein the stent is made from a shape memory alloy and further comprising cooling the stent below its transformation temperature prior to moving the plunger and outer tube relative to each other such that the stent is pulled into and disposed within the outer tube.

23. A method inserting a stent into a deployment catheter, said deployment catheter comprising an outer tube, a plunger at least partially disposed within said outer tube and having a longitudinal dimension, and a stent engagement device connected to a distal portion of the plunger that engages a proximal end of a stent such that the stent engagement device is expandable away from the longitudinal dimension of the plunger, comprising:
   a) permitting the stent engagement device to expand away from the longitudinal dimension of the plunger;
   b) passing the deployment catheter through the center of a funnel;
   c) cooling the stent;
   d) engaging the stent engagement device and a proximal end of the stent;
   e) while maintaining the engagement of the stent engagement device and the stent, positioning the deployment catheter relative to the funnel such that the funnel maintains the engagement of the stent engagement device and the stent; and
   f) moving the plunger and outer tube relative to each other such that the stent is pulled into and disposed within the outer tube.

24. The method as claimed in claim 23 wherein the stent further comprises a catheter engagement device connected to its proximal end and wherein the stent engagement device engages the catheter engagement device.

25. The method as claimed in claim 24 wherein the catheter engagement device comprises substantially V-shaped elements.

26. The method as claimed in claim 25 wherein the stent engagement device comprises one or more hook-like elements connected to a distal portion of the plunger.

27. The method as claimed in claim 26 wherein the stent engagement device and the catheter engagement device are engaged by compressing the proximal end of the stent so as to hook the V-shaped elements onto the hook-like elements such that a force applied to the plunger along the lengthwise axis of the deployment catheter away from a distal end of the deployment catheter pulls the stent in the same direction as the force.

28. The method as claimed in claim 26 wherein the stent comprises a plurality of parallel struts connected by a plurality of connecting members and wherein the catheter engagement device comprises hooks having two ends each of which is attached to the proximal end of an adjacent stent strut.

29. The method as claimed in claim 23 wherein the stent is made from a shape memory alloy and further comprising cooling the stent below its transformation temperature prior to moving the plunger and outer tube relative to each other such that the stent is pulled into and disposed within the outer tube.

30. A stent deployment catheter comprising an outer tube, a plunger at least partially disposed within said outer tube and having a longitudinal dimension, and a stent engagement means being outwardly biased by a coil portion connected to a distal end of the plunger for engaging a proximal end of a stent the stent engagement means being outwardly biased such that the stent engagement means expands away from the longitudinal dimension of the plunger, wherein the stent engagement means comprises one or more hook-like elements.

31. The stent deployment catheter as claimed in claim 30 wherein the one or more hook-like elements are connected to a distal portion of the plunger.

32. The stent deployment catheter as claimed in claim 31 wherein the hook-like elements project from a distal end of the plunger.

33. The stent deployment catheter as claimed in claim 30 wherein the engagement means comprises a tubular body having a distal surface.

34. The stent deployment catheter of claim 30, the stent engagement means comprises a coiled portion.

* * * * *

UNITED STATES PATENT AND TRADEMARK OFFICE
CERTIFICATE OF CORRECTION

PATENT NO. : 6,776,791 B1
DATED : August 17, 2004
INVENTOR(S) : Jody W. Stallings and Frederick Ahari It is certified that error appears in the above-identified patent and that said Letters Patent is hereby corrected as shown below:

Column 5,
Line 36, delete "apposition" and insert -- a position --.

Signed and Sealed this

First Day of March, 2005

JON W. DUDAS
*Director of the United States Patent and Trademark Office*